United States Patent [19]

Black

[11] Patent Number: 5,531,740
[45] Date of Patent: Jul. 2, 1996

[54] AUTOMATIC COLOR-ACTIVATED SCANNING TREATMENT OF DERMATOLOGICAL CONDITIONS BY LASER

[75] Inventor: Michael Black, Foster City, Calif.

[73] Assignee: Rapistan Demag Corporation, Grand Rapids, Mich.

[21] Appl. No.: 300,969

[22] Filed: Sep. 6, 1994

[51] Int. Cl.$^6$ ................................................ A61B 17/36
[52] U.S. Cl. ...................................................... 606/9; 606/11
[58] Field of Search ............................. 606/2, 3, 10, 11, 606/12, 13, 17; 607/88, 89

[56] References Cited

U.S. PATENT DOCUMENTS

| | | | |
|---|---|---|---|
| 4,718,417 | 1/1988 | Kittrell et al. | 606/15 |
| 4,848,340 | 7/1989 | Bille et al. | 606/4 |
| 5,057,102 | 10/1991 | Tomioka et al. | 606/4 |
| 5,353,790 | 10/1994 | Jacques et al. | 606/3 |

*Primary Examiner*—Stephen C. Pellegrino
*Assistant Examiner*—Sonya Harris-Ogugua
*Attorney, Agent, or Firm*—Van Dyke, Gardner, Linn & Burkhart

[57] ABSTRACT

A method and apparatus are disclosed for automatically delivering a laser beam [30] to an intricate colored region [23] of a treatment area [32], e.g. for laser photocoagulation treatment of venular malformations and other dermatological conditions. Reflected light from the treatment area [32] travels into the delivery console [28] to a color-sensitive detector which signals a control system to permit the laser beam [30] to be delivered to the treatment area [32] only when the beam is focused on a spot having a predetermined color. By scanning over the treatment region, the laser automatically treats only the area having a specified color. Since reflective optics are employed, the reflected light precisely indicates the color of the region where the treatment beam is focused. Reflective optics also provide a smaller and more precise spot size for the treatment beam.

8 Claims, 4 Drawing Sheets

AUTOMATIC COLOR-ACTIVATED SCANNING TREATMENT OF DERMATOLOGICAL CONDITIONS BY LASER

BACKGROUND—FIELD OF THE INVENTION

This invention relates to methods and devices for treating objects with laser beams, specifically to methods and devices for laser photocoagulation treatment of venular malformations and other dermatological conditions.

BACKGROUND—PRIOR ART

Among their many medical applications, lasers are used for photocoagulation treatment of venular malformations, such as port wine stains, varicose veins, and spider veins. In these applications a laser beam is delivered to the malformed veins, causing their photocoagulation. This is presently the preferred method of treatment for these conditions.

Since laser beams can damage and potentially scar healthy tissue, it is especially important that the laser beam be precisely directed only to the malformed veins themselves.

In many cases, however, the venular malformation to be treated forms an extremely intricate pattern. Moreover, the veins in question can be as small as 0.1 mm in diameter. Consequently, the task of precisely delivering the laser beam exclusively to the venular malformation becomes quite formidable.

The conventional means for treating an intricate area with a laser beam is either by manual guidance or by preprogramming the laser system with a precise coordinate description of the treatment area.

Manual control of the laser beam has several obvious disadvantages. Since the treatment area is so small and intricate, manual control is very time consuming and labor intensive. Moreover, manual control easily results in accidental damage to healthy skin due to involuntary movements of the hand, especially in the case of veins as small as 0.1 mm.

The problems caused by involuntary hand movements can be solved by using an automated laser system that is preprogrammed to precisely treat the intricate pattern of veins. This method, however, is even more time consuming and labor intensive than manual control since the pattern must be encoded as a coordinate description to be programmed into the automated laser control system. In addition, since no two patients have the same pattern of veins, a different pattern must be programmed into the laser system each time.

In addition to the above difficulties associated with present methods for precisely controlling the delivery of a laser beam to an intricate area, there is also a difficulty with present laser systems themselves. Most laser systems employ refractive (lens-based) optics to guide and focus the laser beam. Refractive optics, however, presently can not be focused to a spot size smaller than 0.4 mm (Coherent, Inc. micromanipulator, model 5000). Consequently, when treating veins as small as 0.1 mm in diameter, present laser systems unnecessarily damage and scar proximate healthy tissue.

OBJECTS AND ADVANTAGES

Accordingly, it is an object of the present invention to provide a method and apparatus for quickly and simply treating venular malformations without unnecessarily scarring healthy tissue. Unwanted scarring is reduced by providing a more precise beam delivery system that can focus beams to a very small diameter. Scarring is further reduced by automated control of the laser delivery device, thus providing precise and stable delivery of the beam, and eliminating involuntary exposure of proximate tissue. Further objects and advantages of this invention will become apparent from a consideration of the ensuing description and accompanying drawings.

SUMMARY OF THE INVENTION

The quick and simple treatment of intricate patterns is accomplished by means of a feedback circuit that employs color-discriminating detectors that indicate the color of the region upon which the laser is focused. As the apparatus systematically scans an area enclosing the intricate pattern of veins, the treatment beam is activated only when the laser is focused on a region of skin having a predetermined color, e.g., the red color of a varicose vein. This color-activated method of treatment eliminates the time-consuming procedure of manually tracing the treatment area or preprogramming a computer to trace the treatment area. Finally, undesired scarring is reduced by improved focusing using mirror-based beam delivery as is used in this inventor's micromanipulator (U.S. Pat. No. 5,128,509 issued 7 Jul. 1992).

BRIEF DESCRIPTION OF DRAWING FIGURES

Figure 1:
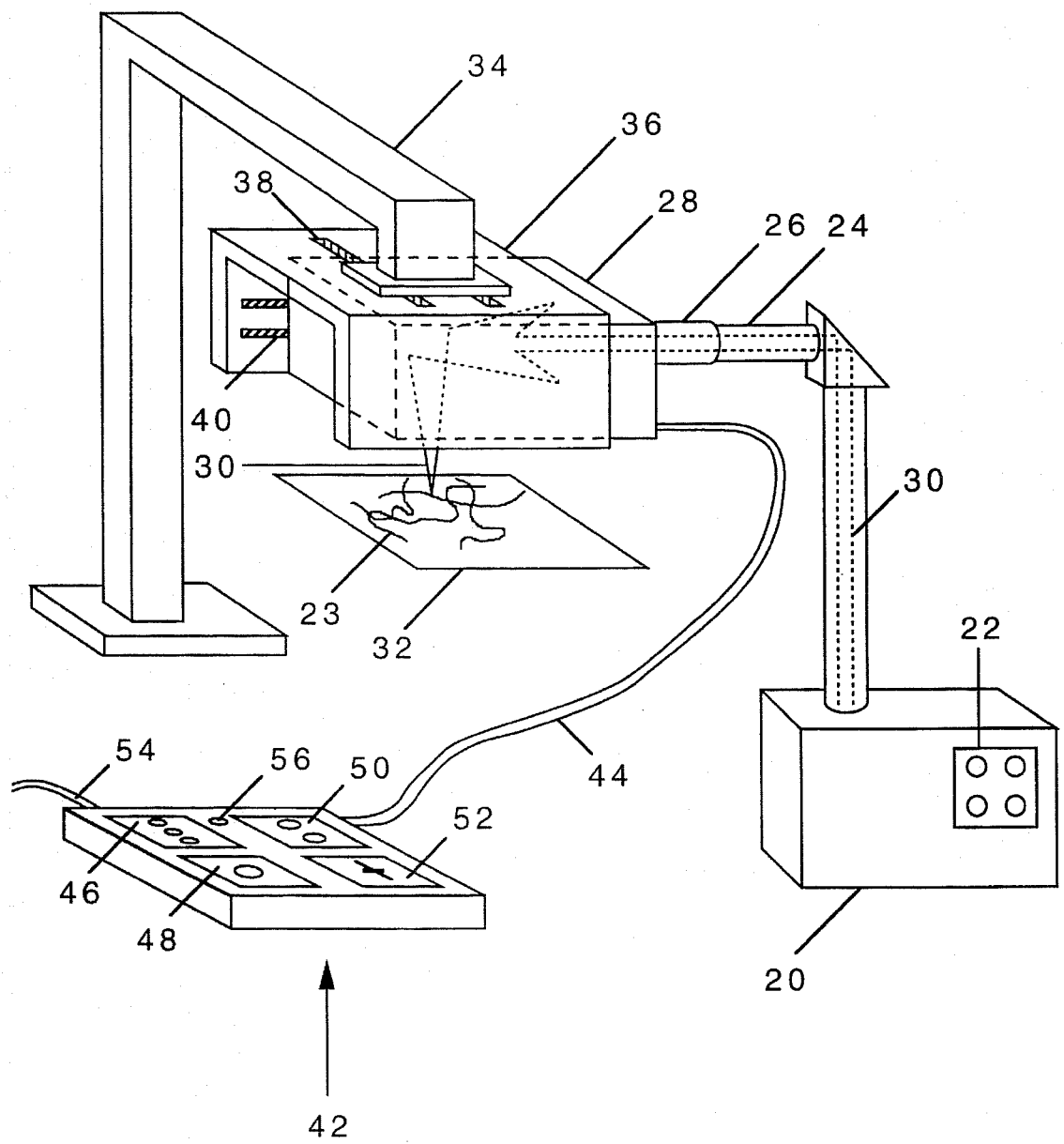
FIG. 1 is a perspective view of the apparatus together with a conventional laser and a treatment area.

REFERENCE NUMERALS IN DRAWINGS 20 laser
22 laser controls
23 intricate colored region
24 articulated arm
26 laser adapter
28 beam delivery console
30 laser beam
32 treatment area
34 support arm
36 outer casing
38 Y-motion rails
40 X-motion rails
42 control panel
44 cable
46 BGR color selector
48 scanner speed selector
50 scanner X-Y selector
52 shutter speed selector
54 power supply
56 power switch
58 shutter
59 beam splitter
60 passage hole
62 concave mirror
64 convex mirror 66 flat mirror
68 aperture
70 illumination source
72 reflected light
73 rotating disk
74 photodiode detector
76 photodiode detector
78 photodiode detector
80 photodiode detector
82 red filter
84 green filter
86 blue filter
88 white reference filter
90 amplifier
92 amplifier
94 amplifier
96 amplifier
98 differential amplifier
100 differential amplifier
102 differential amplifier
104 trigger
106 trigger
108 trigger
110 control system
112 X-Y motion control

DETAILED DESCRIPTION —FIG. 1

FIG. 1 shows a preferred embodiment of an apparatus according to the invention. A conventional laser 20 with laser controls 22 is used to photocoagulate veins or the like which form an intricate colored region 23 on a treatment area 32 of a patient (not shown). An articulated arm 24, a laser adapter 26, and a beam delivery console 28 guide a laser beam 30 to a treatment area 32. For example, laser 20 may be a conventional flashlamp-pumped pulsed dye laser generating a laser beam 30 with pulsewidths of 300 to 450 milliseconds for photocoagulation treatment of venular malformation in treatment area 32.

A support arm 34 fixed above treatment area 32 is connected to an outer casing 36 by means of Y-motion rails 38 allowing outer casing 36 to move in the Y-direction. Beam delivery console 28 is similarly connected to outer casing 36 by means of X-motion rails 40 allowing console 28 to move in the X-direction. Small motors (not shown) control the X-Y position of console 28 and hence allow beam 30 to be accurately positioned above area 32.

Console 28 is connected to a control panel 42 by a cable 44. Panel 42 includes four controls: a BGR (blue, green, and red) color selector 46, a scanner speed selector 48, a scanner X-Y selector 50 and a shutter speed selector 52. In addition, the control panel has a power supply 54 and a power switch 56.

DETAILED DESCRIPTION—FIG. 2

Figure 2:
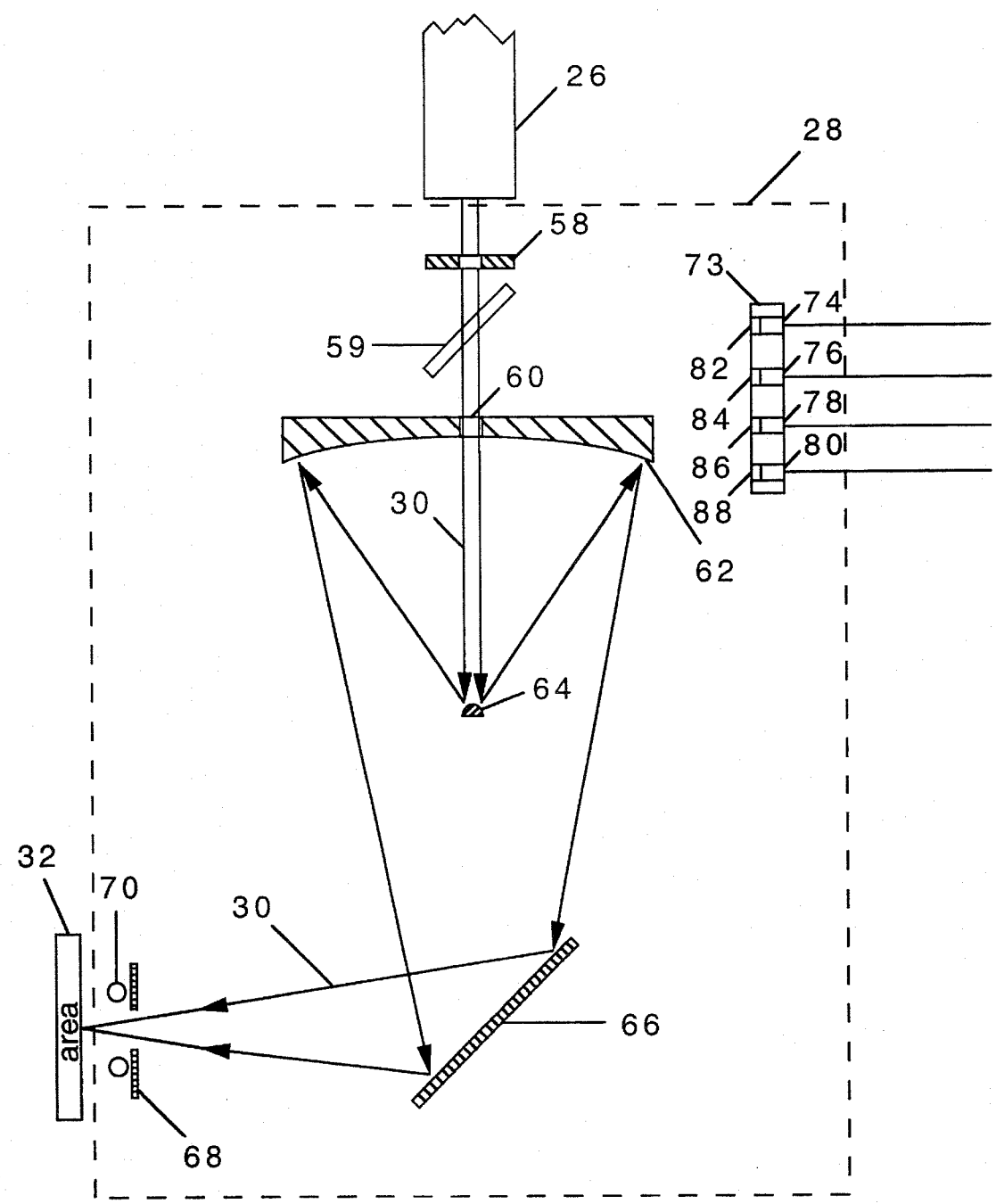
FIG. 2 is a cross-sectional view of the apparatus detailing the interior of the beam delivery console when the laser shutter is open.

FIG. 2 is a cross-sectional view showing the interior of console 28 when shutter 58 is open. After emerging from laser adapter 26, beam 30 passes through beam splitter 59, shutter 58, and then through a passage hole 60 located in the center of a concave mirror 62. Beam 30 then reflects from a convex mirror 64 which directs the beam backward in a diverging manner toward mirror 62. Mirror 62 then reflects diverging beam 30 back toward mirror 64 in a converging manner. Since the width of beam 30 is much larger than the width of mirror 64, nearly all of beam 30 passes around mirror 64. Converging beam 30 then reflects from a flat mirror 66, passes through an aperture 68, and falls upon area 32. In this manner, shutter 58 controls whether beam 30 will be delivered to area 32. Shutters such as this are available commercially from Uniblitz of Rochester, N.Y.

DETAILED DESCRIPTION—FIG. 3

Figure 3:
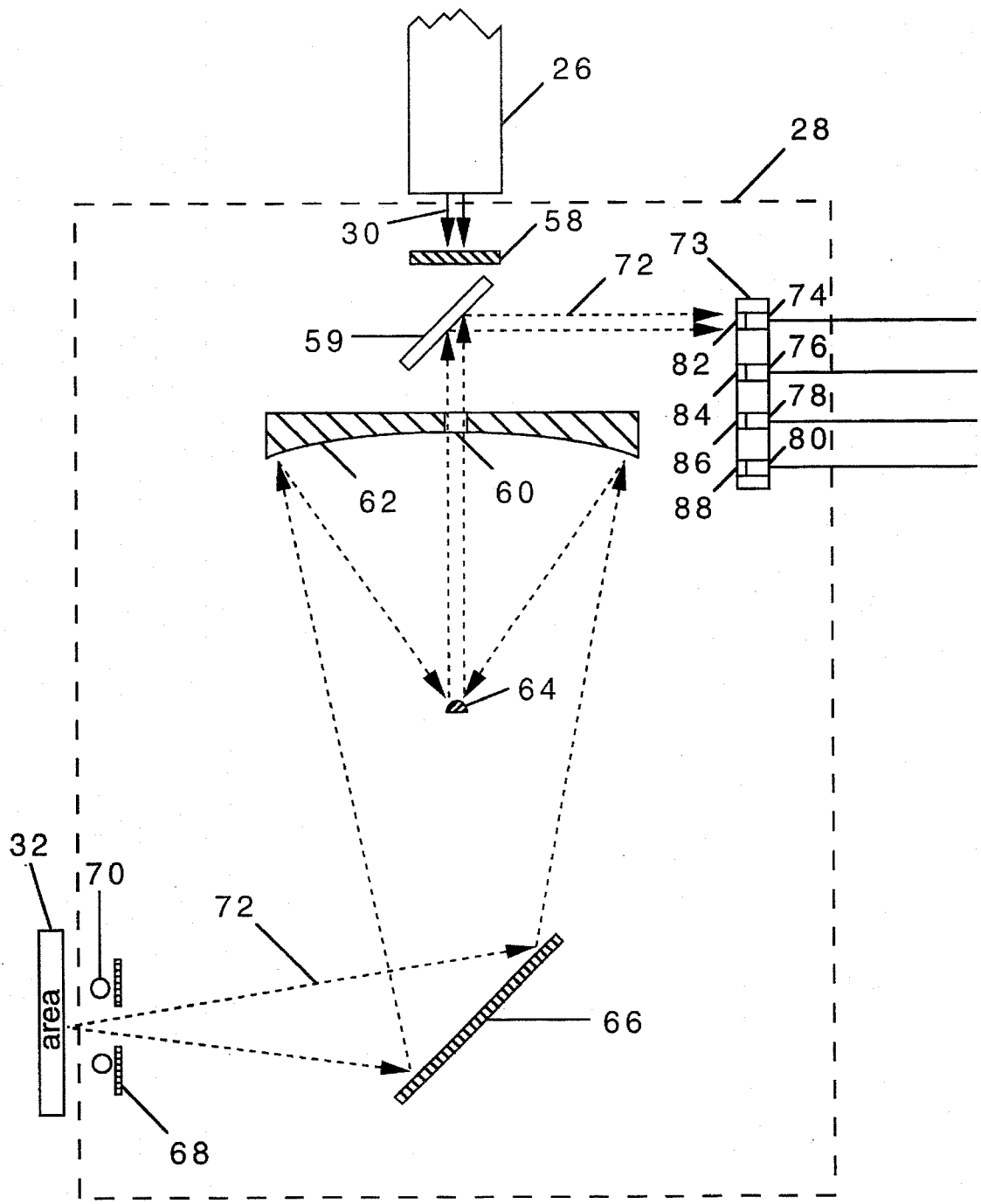
FIG. 3 is a cross-sectional view of the apparatus detailing the interior of the beam delivery console when the laser shutter is closed.

FIG. 3 is an identical cross-sectional view showing the interior of console 28 when shutter 58 is closed. Since shutter 58 blocks the passage of beam 30, area 32 is irradiated only by the white light from an illumination source 70 which encircles aperture 68 just above area 32. Reflected light 72 from area 32 passes through aperture 68, reflects from flat mirror 66, from concave mirror 62, from convex mirror 64, and through passage hole 60. Between passage hole 60 and shutter 58 is positioned a beam splitter 59 which is composed of a material that transmits light frequencies such as that of beam 30 (FIG. 2) while reflecting light frequencies such as that of reflected light 72. Consequently, reflected light 72 is directed by beam splitter 59 to a rotating disk 73.

Embedded within rotating disk 73 are four photodiode detectors 74, 76, 78, and 80. Detectors 74, 76, 78, and 80 are positioned just behind a red filter 82, a green filter 84, a blue filter 86, and a white reference filter 88. As rotating disk 73 rotates, reflected light 72 passes successively through filters 82, 84, 86, and 88, and is detected by detectors 74, 76, 78, and 80, whose signals can then be used to precisely determine the color of the area upon which beam 30 is focused. Photodiode detectors such as these are commercially available from Hamamatsu of Hamamatsu City, Japan.

Note that since reflective optics are used, reflected light 72 follows the same path as beam 30 (FIG. 2) albeit in the reverse direction, in spite of their different frequencies.

As a result, color detectors 74, 76, 78, and 80 precisely indicate only the color of the small area where the treatment beam is focused. Moreover, reflective optics allows focusing of the treatment beam to a spot size of 0.1 mm or less, thus improving the precision of the treatment by a factor of two over prior methods.

DETAILED DESCRIPTION —FIG. 4

Figure 4:
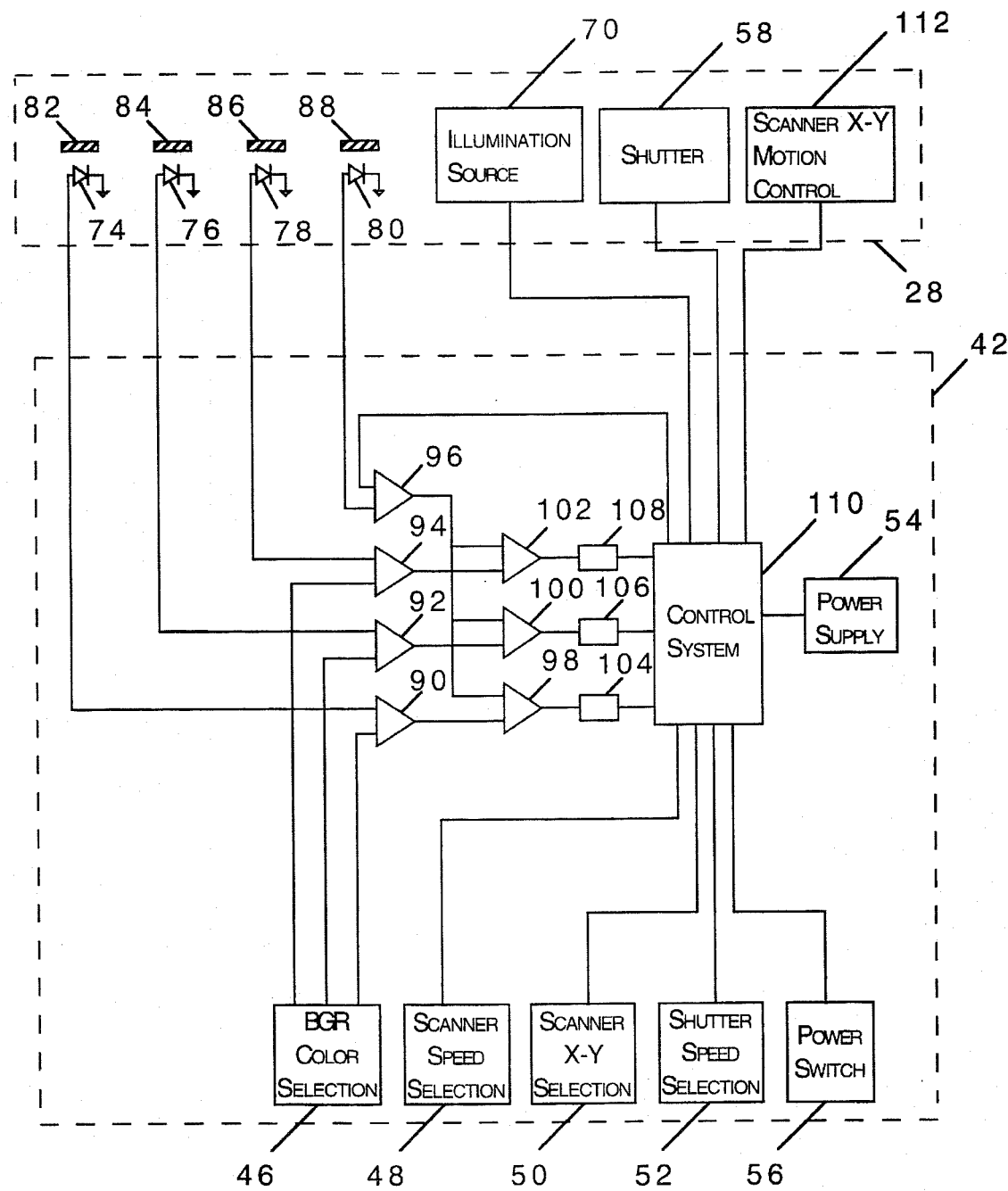
FIG. 4 is a schematic diagram of the apparatus.

FIG. 4 is a schematic diagram detailing the manner in which the signals from the four detectors are combined to trigger delivery of the laser beam. Four amplifiers 90, 92, 94, and 96 amplify signals from detectors 74, 76, 78, and 80, respectively. The amount of amplification of the signals from color detectors 74, 76, and 78 is determined by the amplification settings from the BGR color selector 46 in control panel 42. The amplification of signals from white light detector 80 is fixed at a predetermined calibration level. Signals from color amplifiers 90, 92, and 94 are compared with the reference signals from white light amplifier 96 by three differential amplifiers 98, 100, and 102, respectively. Each differential amplifier can activate one of three triggers 104, 106, and 108. Control system 110 then sends a signal to open shutter 58 when any one of triggers 104, 106, and 108 is activated, indicating that laser beam 30 is focused on the intricate colored region 23 of area 32 with the appropriate preselected color.

DETAILED DESCRIPTION—OPERATION

To operate the device, the operator begins by setting the various selections of the control panel 42 (FIG. 1). The BGR color selector 46 is set to the desired color corresponding to the area to be treated. If needed, the color of the area to be treated can be enhanced by a color marking pen. The scanner speed selector 48 and the shutter speed selector 52 are set automatically. If required, the X-Y position can be manually set with the scanner X-Y selector. Laser 20 is set to the appropriate operating frequency, power, and pulse mode by controls 22. Finally, area 32 is immobilized beneath beam delivery console 28.

Once panel 42 and laser 20 are set, the device begins to systematically scan area 32, treating appropriate areas as they are encountered. If beam 30 is focused over an area having the appropriate color, shutter 58 is opened and the area is treated. Shutter 58 then closes and scanner X-Y motion control 112 moves console 28, and hence the focus of laser beam 30, to the adjacent area. Since console 28 systematically scans over area 32, the intricate colored region 23 of area 32 is automatically treated with beam 30, leaving the other areas unaffected.

Conclusions, Ramifications, and Scope

Thus it is evident that this apparatus provides a method for quickly and simply treating venular malformations without unnecessarily scarring healthy tissue. Scarring is minimized by providing improved focusing of laser energy and providing automatic control of the laser beam delivery. Moreover, by positioning color-discriminating detectors within the delivery optics of the device, the method may be used to quickly and simply treat an intricate pattern with high precision.

While the above descriptions contain many specificities, these should not be construed as limitations on the scope of the invention, but as merely illustrating a particular embodiment thereof. Many other variations are possible. For example, the principle of the device may be applied to other dermatological treatments, such as tattoo removal; it may be applied to other medical treatments, as in ophthalmology; moreover, it may be used in numerous non-medical procedures as well, such as welding, soldering, and etching.

Clearly, many details of the described embodiment may be varied. There may be any number of color detectors positioned on the rotating disk. Rather than using a beam splitter to direct the reflected light to the rotating disk, the rotating disk may be connected to one side of the shutter. Rather than using a rotating disk, the beam splitter may be moved to direct the reflected light to the four photodiodes. Alternatively, a prism or other optical element may be used to disperse the reflected light over the area of all four detectors. The detectors and filters can be chosen to detect any desired frequencies of light reflected from the treatment area, including ultraviolet and infrared light.

The laser may be one of many different commercial lasers available for generating a laser beam having any of many different wavelengths, or it may be a tunable laser capable of producing laser beams in a continuous range of wavelengths. In particular, the apparatus may be set to simultaneously treat several different intricate colored regions with different laser frequencies by a simple connection between the console and laser controls. Moreover, the light beam used for treatment may be generated from a light source that is not a laser, such as a flashlamp.

The laser beam can be sent to the beam delivery console by fiber optics as well as by an articulated arm, or it may be integrated within the console itself. The optics in the beam delivery console may be composed of various combinations of mirrors which serve to guide the laser beam. In particular, the flat mirror used in the preferred embodiment may be eliminated. The method illustrated for analyzing the detector signals outlines just one of many possible circuits for accomplishing the same task. The mechanical arrangement described for allowing x-y motion of the delivery optics may be replaced by any one of many other such mechanical means.

Accordingly, the scope of the invention should be determined not by the embodiment illustrated, but by the appended claims and their legal equivalents.

I claim:

1. A method for delivering a light beam from a light source to a colored region of a treatment area having a predetermined color, said method comprising:

guiding said light beam along an optical path from said light source to a region on said treatment area, positioning in said optical path a shutter for interrupting the delivery of said light beam to said area, visibly illuminating said area with an illumination source thereby generating reflected light from said area, positioning in said optical path between said shutter and said area a color-discriminating detector means for detecting the color of said reflected light, opening said shutter by a control system when said color-discriminating detector means indicates that said reflected light from said area has said predetermined color, adjusting said optical path with an X–Y motion control means so that said light beam is guided to a surface of said treatment area, whereby said laser beam is delivered only to said region of said treatment area having a predetermined color as said reflective optical system scans over the entire surface of said treatment area.

2. The method of claim 1 wherein said light source is a laser, said light beam is a laser beam, and said optical path includes a reflective optical system comprising an articulated arm for guiding said laser beam from said laser to a beam delivery console having an interior, a laser adapter for launching said laser beam into the interior of said delivery console, a concave mirror with a central passage hole through which said laser beam passes, said concave mirror oriented with a reflective side facing said laser beam passing through said central passage hole, a convex mirror whose reflective surface faces the reflective side of said concave mirror, said convex mirror positioned to direct said laser beam back toward said concave mirror, and a flat mirror for redirecting said laser beam from said concave mirror through an angle substantially equal to 90 degrees.

3. The method of claim 2 wherein said color-discriminating detector means is positioned between said shutter and said central passage hole and comprises a rotating disk, a beam splitter which directs said reflected light to said rotating disk, four photodiodes embedded in said rotating disk, and four filters, each of which positioned adjacent to said four photodiodes, each of said filters being arranged to transmit a different wavelength of light.

4. The method of claim 3 wherein one of said filters transmits only substantially red light, one of said filters transmits only substantially green light, one of said filters transmits only substantially blue light, and one of said filters transmits only substantially white light.

5. An apparatus for delivering a light beam to a region of a treatment area having a predetermined color, said apparatus comprising:

a light source for generating and delivering said light beam, said light beam creating an optical path from said light source to a region on said treatment area, a shutter positioned in said optical path for interrupting the delivery of said light beam to said area, an illumination source for visibly illuminating said area, thereby generating reflected light from said area, a color-discriminating detector means positioned in said optical path between said shutter and said area for detecting the color of said reflected light, a control system for opening said shutter when said color-discriminating detector means indicates that said reflected light from said area has said predetermined color, an X–Y motion control means for adjusting said optical path to guide said light beam to a surface of said treatment area, whereby said light beam is delivered to said region of said treatment area having a predetermined color as said optical path scans over the surface of said treatment area.

6. The apparatus of claim 5 wherein said light source is a laser, said light beam is a laser beam, and said optical path includes a reflective optical system comprising an articulated arm for guiding said laser beam from said laser to a beam delivery console having an interior, a laser adapter for launching said laser beam into the interior of said delivery console, a concave mirror with a central passage hole through which said laser beam passes, said concave mirror oriented with a reflective side facing said laser beam passing through said central passage hole, a convex mirror whose reflective surface faces the reflective side of said concave mirror, said convex mirror positioned to direct said laser beam back toward said concave mirror, and a flat mirror for redirecting of said laser beam from said concave mirror through an angle substantially equal to 90 degrees.

7. The apparatus of claim 6 wherein said color-discriminating detector means is positioned between said shutter and said central passage hole and comprises a rotating disk, a beam splitter which directs said reflected light to said rotating disk, four photodiodes embedded in said rotating disk, and four filters, each of which positioned adjacent to said four photodiodes, each of said filters being arranged to transmit a different wavelength of light.

8. The apparatus of claim 7 wherein one of said filters transmits only substantially red light, one of said filters transmits only substantially green light, one of said filters transmits only substantially blue light, and one of said filters transmits only substantially white light.

* * * * *

UNITED STATES PATENT AND TRADEMARK OFFICE
CERTIFICATE OF CORRECTION

PATENT NO. : 5,531,740

DATED : Jul. 2, 1996

INVENTOR(S) : Michael Black

It is certified that error appears in the above-identified patent and that said Letters Patent is hereby corrected as shown below:

On title page, item [73] should read as follows:
--Reliant Technologies, Inc. Foster City, Calif.

Attorney, Agent, or Firm - no name should be printed.

Signed and Sealed this

Tenth Day of September, 1996

*Attest:*

BRUCE LEHMAN

*Attesting Officer*     *Commissioner of Patents and Trademarks*